US008557854B2

(12) United States Patent
Van 'T Klooster et al.

(10) Patent No.: US 8,557,854 B2
(45) Date of Patent: Oct. 15, 2013

(54) USE OF A SULFONAMIDE COMPOUND FOR IMPROVING THE PHARMACOKINETICS OF A DRUG

(75) Inventors: Gerben Albert Van 'T Klooster, Le Breda (NL); Piet Tom Bert Paul Wigerinck, Terhagen (BE); Sandra De Meyer, Beerse (BE); Lieven Elvire Colette Baert, Bruges (BE); Herman Augustinus De Kock, Arendonk (BE)

(73) Assignee: Janssen R&D Ireland, Little Island Co, Cork (IE)

( * ) Notice: Subject to any disclaimer, the term of this patent is extended or adjusted under 35 U.S.C. 154(b) by 448 days.

(21) Appl. No.: 11/911,465

(22) PCT Filed: Apr. 14, 2006

(86) PCT No.: PCT/EP2006/061614
§ 371 (c)(1),
(2), (4) Date: Jun. 10, 2008

(87) PCT Pub. No.: WO2006/108879
PCT Pub. Date: Oct. 19, 2006

(65) Prior Publication Data
US 2008/0287488 A1  Nov. 20, 2008

Related U.S. Application Data

(60) Provisional application No. 60/684,283, filed on May 25, 2005.

(30) Foreign Application Priority Data

Apr. 15, 2005 (EP) .................................. 05103035

(51) Int. Cl.
*A61K 31/423* (2006.01)
*C07D 277/24* (2006.01)
(52) U.S. Cl.
USPC .......................................... 514/365; 548/204
(58) Field of Classification Search
USPC ........................................................ 548/204
See application file for complete search history.

(56) References Cited

U.S. PATENT DOCUMENTS

2002/0039998 A1  4/2002  Norbeck et al.

FOREIGN PATENT DOCUMENTS

| WO | WO 99/33792 A2 | 7/1999 |
|---|---|---|
| WO | WO 99/33795 A1 | 7/1999 |
| WO | WO 99/33815 A1 | 7/1999 |
| WO | WO 02/083657 A2 | 10/2002 |
| WO | WO 02/092595 A1 | 11/2002 |
| WO | WO 03/033793 A1 | 4/2003 |
| WO | WO 03/049746 A2 | 6/2003 |
| WO | WO 03/090690 A3 | 11/2003 |
| WO | WO 2005/030739 A1 * | 4/2005 |

OTHER PUBLICATIONS

Cytochrome P450 [online] retrieved on Jun. 30, 2010 from the internet. URL; http://en.wikipedia.org/wiki/Cytochrome_P450.*
Augustijns, P., et al. "Drug Absorption Studies of Prodrug Esters Using the Caco-2 Model: Evaluation of Ester Hydrolysis and Transepithelial Transport", International Journal of Pharmaceutics (1998) vol. 166, pp. 45-53.
Borst, P., et al. "The Multidrug Resistance Protein Family", Biochimica et Biophysica Acta (1999) vol. 1461, pp. 347-357.
Godman and Gilman, "The Pharmacological Basis of therapeutics", Eighth Edition, Chapter 11, "Biotransformmation of Drugs", pp. 13-15.
Sulkowski, M., et al. "Hepatotoxicity Associated With Antiretroviral Therapy in Adults Infected With Human Immunodeficiency Virus and the Role of Hepatitis C or B Virus Infection", JAMA (2000) vol. 283, No. 1, pp. 74-80.
International Search Report for corresponding Application No. PCT/EP2006/061614 mailed Nov. 6, 2006.
Ernest II, C.S., et al., "Mechanism-Based Inactivation of CYP3A by HIV Protease Inhibitors", The Journal of Pharmacology and Experimental Therapeutics, (2006), vol. 312, No. 2, pp. 583-591.
Moltke, L., et al., "Potent Mechanism-Based Inhibition of Human CYP3A in Vitro by Amprenavir and Ritonavir: Comparison With Ketoconazole", Eur. J. Pharmacol (2000), vol. 56, pp. 259-261.
Shibata, N., et al., "In-Vitro and In-Vivo Pharmacokinetic Interactions of Amprenavir, an HIV Protease Inhibitor, With Other Current HIV Protease Inhibitors in Rats", Journal of Pharmacy and Pharmacology, (2001), vol. 54, No. 2, pp. 221-229.
Flexner, Charles, "Dual Protease Inhibitor Therapy in HIV-Infected Patients: Pharmacologic Rationale and Clinical Benefits", Annu. Rev. Pharmacol Toxicol, (2000), vol. 40, pp. 649-674.

* cited by examiner

*Primary Examiner* — Shawquia Young
(74) *Attorney, Agent, or Firm* — Michael J. Atkins

(57) ABSTRACT

A method for improving the pharmacokinetics of drugs, which are metabolized by cytochrome P450 monooxygenase is disclosed. More specifically it relates to a method for improving the pharmacokinetics of retroviral protease inhibitors and in particular for improving the pharmacokinetics of human immunodeficiency virus (HIV) protease inhibitors. A pharmaceutical composition and its use in the manufacture of a medicament for the inhibition or treatment of an HIV infection or AIDS in a human being are also part of the invention.

1 Claim, 1 Drawing Sheet

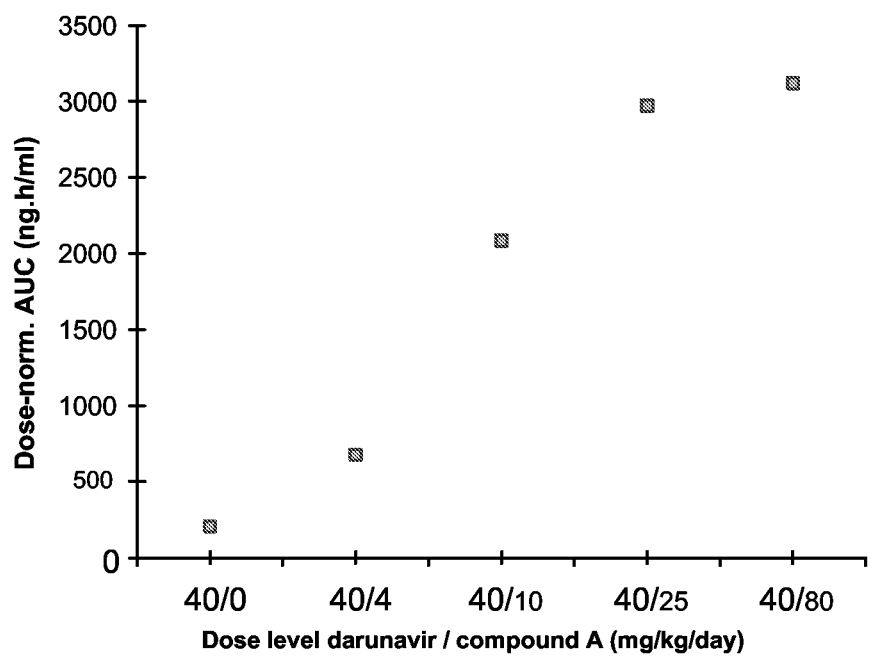

USE OF A SULFONAMIDE COMPOUND FOR IMPROVING THE PHARMACOKINETICS OF A DRUG

CROSS REFERENCE TO RELATED APPLICATIONS

This application is the national stage of PCT Application No PCT/EP2006/061614, filed 14 Apr. 2006, which claims priority from European Patent Application No. EP 05103035.1, filed 15 Apr. 2005, and U.S. Application No. 60/684,283, filed 25 May 2005, the entire disclosures of which are hereby incorporated in their entirely.

The present invention relates to a method for improving the pharmacokinetics of drugs, which are metabolized by cytochrome P450 monooxygenase. More specifically the present invention relates to a method for improving the pharmacokinetics of retroviral protease inhibitors and in particular for improving the pharmacokinetics of human immunodeficiency virus (HIV) protease inhibitors. The invention further relates to a pharmaceutical composition and its use in the manufacture of a medicament for the inhibition or treatment of an HIV infection or AIDS in a human being.

The virus causing the acquired immunodeficiency syndrome (AIDS) is known by different names, including T-lymphocyte virus III (HTLV-III) or lymphadenopathy-associated virus (LAV) or AIDS-related virus (ARV) or human immunodeficiency virus (HIV). Up until now, two distinct families have been identified, i.e. HIV-1 and HIV-2. Hereinafter, HIV will be used to generically denote these viruses.

Different classes of anti-HIV compounds have been marketed so far: Nucleoside Reverse Transcriptase Inhibitors (NRTIs), Non-Nucleoside Reverse Transcriptase Inhibitors (NNRTIs), one Nucleotide Reverse Transcriptase Inhibitor (NtRTI), one Fusion Inhibitor, and Protease Inhibitors (PIs). A triple regimen is considered standard of care and when effective, results in suppression of the virus below viral load detection limits of the current viral load tests, thereby strongly reducing the emergence of resistance and improving the quality of life of the patient.

One of the critical pathways in a retroviral life cycle is the processing of polyprotein precursors by aspartic protease. In HIV, for instance, the gag-pol protein is processed by HIV protease. The correct processing of the precursor polyproteins by the aspartic protease is required for the assembly of infectious virions, thus making the aspartic protease an attractive target for antiviral therapy. In particular for HIV treatment, the HIV protease is an attractive target.

Inhibitors of HIV protease have become cornerstones in the treatment of HIV disease, particularly in patients with a long history of antiretroviral therapy, and the introduction of PIs (protease inhibitors) has led to a major breakthrough in the treatment of HIV-1 infection, substantially reducing morbidity and mortality in infected individuals. Their long-term use, however, is hampered by different factors:
- sub-optimal compliance due to a high pill burden and food restrictions, especially for single PI regimens without co-administration of low dose ritonavir or dual PI regimens.
- side effects (e.g. lipodystrophy, metabolic abnormalities) with severe impact on the quality of life, and
- the emergence of HIV isolates that are no longer inhibited by the PIs used, and in many cases also resistant to other currently known PIs due to the high level of cross-resistance within this class.

All currently available protease inhibitors (PIs) have pharmacokinetic profiles that limit their efficacy.

Protease inhibitors (PIs) and non-nucleoside reverse transcriptase inhibitors (NNRTIs) are extensively metabolized by the cytochrome P450 system, as are many other drugs. Cytochrome P450 is a group of enzymes found in the liver and the gut, which have a number of functions in the human body. One function is the breakdown and clearance of medications and other chemicals. Taking two or more drugs, which are metabolized by cytochrome P450, may produce a drug interaction affecting concentrations of one or both drugs, and causing side effects or undermining the clinical efficacy of the medication(s). The activity of cytochrome P450 differs between individuals and between populations. Small genetic variations can affect how many particular enzymes are expressed, and thus how quickly the drug is metabolized.

Cytochrome P450 enzymes which derive from a particular gene are called isoforms. Based on the similarity of their chemical make-up, isoforms are divided into families and subfamilies. Enzyme variants are described through a numbering and lettering system, which reflects their chemical and genetic structure.

Cytochrome P450, subfamily IIIA (niphedipine oxidase), polypeptide 4, also referred to as CYP3A4, is one particular metabolic pathway used for breakdown and clearance of medications and other substances.

Many drugs, including some HIV protease inhibitors, are metabolized by cytochrome P450 monooxygenase, leading to unfavorable pharmacokinetics and the need for more frequent and higher doses than are most desirable. Administration of such drugs with an agent that inhibits metabolism by cytochrome P450 monooxygenase will improve the pharmacokinetics of the drug.

Most HIV protease inhibitors in clinical therapy are now paired with ritonavir to improve exposure and thereby enhancing clinical efficacy. This type of applied drug-drug interaction is referred to as 'boosting'. Boosting also supports simplified treatment regimens for current PIs by reduction of pill burden and frequency of daily intakes.

As a booster, ritonavir, a PI itself, is commonly used at a subtherapeutic dose level of 100 mg twice daily (b.i.d.). Pharmacological enhancement by ritonavir boosting is mediated through inhibition of cytochrome P450 (CYP) 3A4 and drug transporters, specifically P-glycoprotein.

Unfortunately, ritonavir enhancement of PI regimens, even at low doses, is not without risk. Ritonavir toxicity, including gastrointestinal effects, increased risk of hepatotoxicity, and elevations in serum lipids and cholesterol are common. (Sulkowski et al., JAMA, 2000; 283 :74-80). Of these potential side effects, dyslipidemia is the most worrisome as it may potentially increase the risk of cardiovascular and cerebrovascular events.

Thus, there is a high medical need for alternatives to ritonavir as boosting agent in an effective and safe anti-HIV treatment wherein the alternative compounds improve the pharmacokinetic profile of drugs metabolized by cytochrome P450.

In accordance with the present invention it has now been found that compounds having the formula

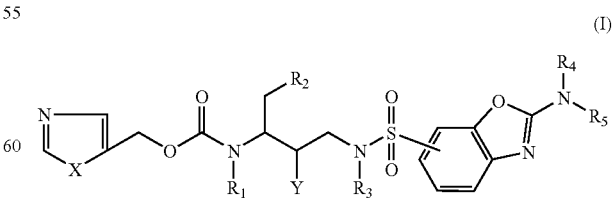

(I)

their N-oxides, salts, stereo-isomeric forms or prodrugs thereof improve the pharmacokinetics of a drug, wherein X represents S; Y represents OH; $R_1$ represents hydrogen; $R_2$ is phenyl; $R_3$ is iso-butyl; $R_4$ is hydrogen and $R_5$ is hydrogen.

Preferred are those compounds having the formula

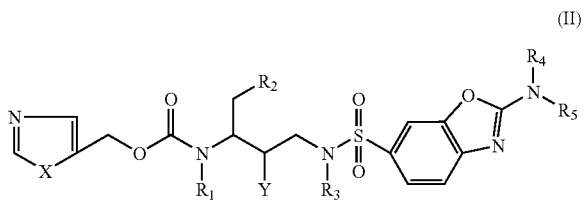
(II)

their N-oxides, salts, stereo-isomeric forms or prodrugs thereof to improve the pharmacokinetics of a drug, wherein X represents S; Y represents OH; $R_1$ represents hydrogen; $R_2$ is phenyl; $R_3$ is iso-butyl; $R_4$ is hydrogen and $R_5$ is hydrogen.

The chemical names and their respective chemical structures of each of the four stereo-isomers of compounds according to formula (II) suitable for use in the current invention are:

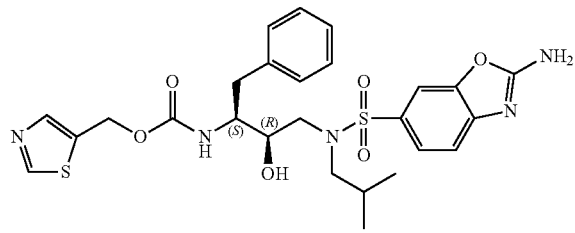
(IIa)

5-thiazolylmethyl[(1S,2R)-3[[(2-amino-6-benzoxazolyl)sulfonyl](2-methylpropyl)amino]-2-hydroxy-1-(phenylmethyl)propyl]carbamate

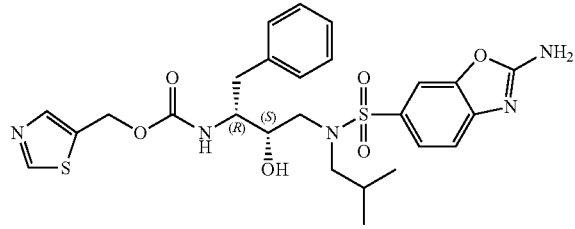
(IIb)

5-thiazolylmethyl[(1R,2S)-3[[(2-amino-6-benzoxazolyl)sulfonyl](2-methylpropyl)amino]-2-hydroxy-1-(phenylmethyl)propyl]carbamate

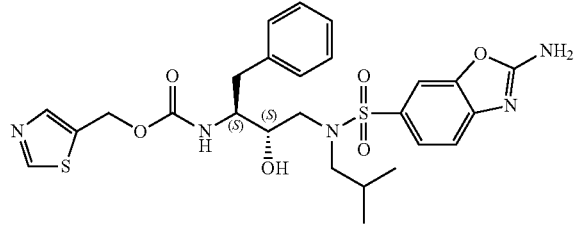
(IIc)

5-thiazolylmethyl[(1S,2S)-3[[(2-amino-6-benzoxazolyl)sulfonyl](2-methylpropyl)amino]-2-hydroxy-1-(phenylmethyl)propyl]carbamate

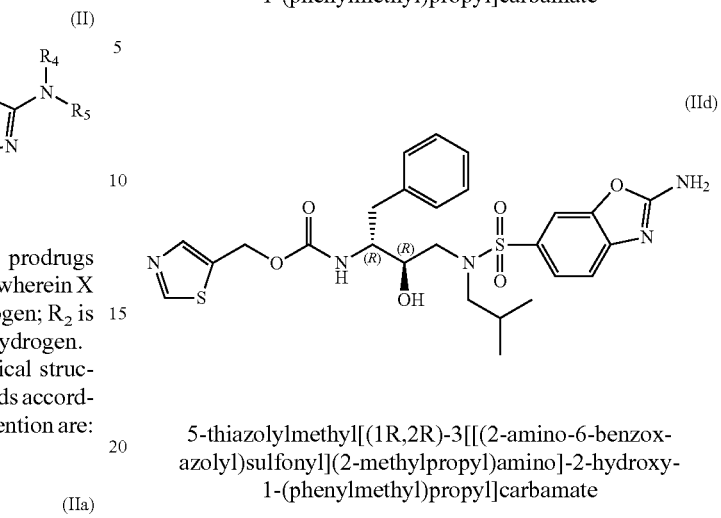
(IId)

5-thiazolylmethyl[(1R,2R)-3[[(2-amino-6-benzoxazolyl)sulfonyl](2-methylpropyl)amino]-2-hydroxy-1-(phenylmethyl)propyl]carbamate In a preferred embodiment of the invention compounds having the formula (I) or (II) are used to improve the pharmacokinetics of a drug wherein said drug is metabolized by cytochrome P450 or more preferably by cytochrome P450 monooxygenase 3A4.

Compounds having the formula (I) or (II) are also used for improving the pharmacokinetics of a drug wherein said drug is inhibited by a transport protein activity such as P-glycoprotein activity. Compounds having the formula (I) or (II) are also used for improving the pharmacokinetics of a drug wherein said drug is inhibited by a multidrug resistance-associated protein efflux channel activity such as MRP1 or MRP2. Multidrug resistance proteins (MRPs) constitute an ATP-binding cassette (ABC) transporter subfamily as identified by Borst et al., (BBA, 1461, 347-357, 1999). MRP1 was the first member described.

Preferred sulfonamide compounds used in the current invention are the compounds having the formula (IIa) or (IIb), most preferred is the compound having the formula (IIa) and is further referred as Compound A.

Compound A, 5-thiazolylmethyl[(1S,2R)-3[[(2-amino-6-benzoxazolyl)sulfonyl]-(2-methylpropyl)amino]-2-hydroxy-1-(phenylmethyl)propyl]carbamate, disclosed in WO 02/092595 has in vitro activity against wild-type HIV-1, and has also activity against a large panel of viruses resistant to currently known PIs.

It has now been found that the compounds of the present invention having the formula (I) and, in particular, formula (II), more in particular having formula (IIa), (IIb), (IIc) or (IId) have unexpected properties.

They, and in particular compound A (formula IIa) and compound E (formula IIb), each increase in rabbits the plasma level of darunavir, a new protease inhibitor under clinical investigation for the treatment of HIV-infections. Darunavir, also referred to as TMC 114, has the following chemical name: (3R,3aS,6aR)-hexahydrofuro[2,3-b]furan-3-yl N-[(1S,2R)-1-benzyl-2-hydroxy-3-(N1-isobutylsulfanilamido)propyl]carbamate.

Saquinavir, another protease inhibitor, is known to be a substrate as well for CYP3A4 metabolism. Low doses of ritonavir have been shown to markedly increase saquinavir plasma concentrations allowing a dosage reduction from 1200 mg t.i.d. when given alone to 1000 mg b.i.d. with 100 mg b.i.d. of ritonavir.

At a range of dose levels, it has now been found that the compounds of the present invention having the formula (I) and, in particular, formula (II), more in particular having formula (IIa), (IIb), (IIc) or (IId) and most preferably compound A (IIa) improve the pharmacokinetic profile of saquinavir in human healthy volunteers.

Preferred dose levels of compounds having formula (I) or (II), in particular compounds having formula (IIa), (IIb), (IIc) or (IId) and more in particular compounds having formula (IIa) or (IIb), ranges from 10-1200 mg/day, preferably from 10-800 mg/day (e.g. 120, 320 or 800 mg/day), more preferably from 20-400 mg/day and even more preferably from 10-150 mg/day. Preferred are those selected from a dose level consisting of 40, 60, 80 or 120 mg/day.

Whenever the term "improving the pharmacokinetics of a drug" is used it is meant (relative to the situation when the drug is administered alone) e.g. enhanced bioavailability of the drug involved in terms of AUC (area under the plasma concentration-time curve), increased blood levels of the drug involved, more specifically an increase of the trough ($C_{min}$) or peak ($C_{max}$) plasma concentration of the drug, or an increase of the half-life of the drug concerned where the increase of said half-life is at least 1× the half-life of the unboosted drug, preferably at least 1.25× the half-life of the unboosted drug, more preferably at least 1.4× or 1.5× the half-life of the unboosted drug and even more preferably at least 1.75× the half-life of said unboosted drug. Most preferred is an increase of at least 2× the half-life of the unboosted drug. For avoidance of doubt the Examples in the current application provide further guidance in this respect.

The term "drug" must be understood broadly and includes among others any compound that is metabolized by cytochrome P450 or is inhibited by a transport protein activity such as P-glycoprotein or is inhibited by a multi-drug resistance-associated protein efflux channel activity such as MRP1 or MRP2 or is a protease inhibitor, preferably a HIV protease inhibitor.

The compounds and drugs as disclosed herein can, if desired, be in the form of a so-called prodrug. "Prodrug" means the pharmacologically acceptable derivatives such as esters, amides and phosphates, such that the resulting in vivo biotransformation product of the derivative is the active compound as defined in formula (I) or (II) or drug concerned. The reference by Goodman and Gilman (The Pharmacological Basis of Therapeutics, 8$^{th}$ ed, McGraw-Hill, Int. Ed. 1992, "Biotransformation of Drugs", p 13-15) describing prodrugs generally is hereby incorporated. Prodrugs of a compound used in the present invention are prepared by modifying functional groups present in the compound in such a way that the modifications are cleaved, either in routine manipulation or in vivo, to the parent compound. Prodrugs include compounds used in the present invention wherein a hydroxy group, for instance the hydroxy group on the asymmetric carbon atom, or an amino group is bonded to any group that, when the prodrug is administered to a patient, cleaves to form a free hydroxyl or free amino, respectively.

Typical examples of prodrugs are described for instance in WO 99/33795, WO 99/33815, WO 99/33793, WO 99/33792 and WO 03/090690 all incorporated herein by reference.

Prodrugs are characterized by improved aqueous solubility relative to the parent compounds, increased bioavailability and are readily metabolized into the active inhibitors in vivo.

An object of the invention is that the drug, when boosted by compounds having the formula (I) or any sub-group thereof, is preferably a protease inhibitor like a HIV protease inhibitor, more specifically a HIV-aspartyl protease inhibitor.

The protease inhibitor is selected from the group consisting of darunavir, amprenavir, fosamprenavir, ritonavir, nelfinavir, saquinavir, indinavir, lopinavir, lasinavir, atazanavir, BMS 186316, DPC 681, DPC 684, tipranavir, AG1776, DMP 450, L 756425, PD178390, PNU 140135 or glycosylation inhibitors such as castanospermine, deoxynojirimycine. In particular, the protease inhibitor is selected from the group consisting of darunavir, amprenavir, fosamprenavir, ritonavir, nelfinavir, saquinavir, indinavir, lopinavir, lasinavir, atazanavir or tipranavir.

Said protease inhibitors, as such, are well known to the skilled person. To give an example lasinavir is 5(S)-(tertbutoxycarbonylamino)-4(S)-hydroxy-6-phenyl-2(R)-(2,3,4-tri-methoxyphenylmethyl)-hexanoyl-N-(2-methoxyethyl) valine amide.

Preferred embodiments for boosting by compounds having the formula (IIa), (IIb), (IIc) or (IId) are those wherein the protease inhibitor is selected from the group consisting of darunavir, amprenavir, fosamprenavir, ritonavir, nelfinavir, saquinavir, indinavir, lopinavir, lasinavir, atazanavir or tipranavir.

The most preferred embodiments for boosting by the compound having formula (IIa) or (IIb) are those wherein the protease inhibitor is darunavir or saquinavir respectively. Even more preferred is the embodiment for boosting by the compound having the formula (IIa) wherein the protease inhibitor is darunavir.

An object of the invention is also a pharmaceutical composition comprising a compound having the formula (IIa), a pharmaceutically acceptable carrier and a drug which is metabolized by cytochrome P450. Said drug in the pharmaceutical composition is preferably a HIV protease inhibitor, more preferably selected from the group consisting of darunavir, amprenavir, fosamprenavir, ritonavir, nelfinavir, saquinavir, indinavir, lopinavir, lasinavir, atazanavir, BMS 186318, DPC 681, DPC 684, tipranavir, AG1776, DMP 450, L 756425, PD178390, PNU 140135 or glycosylation inhibitors such as castanospermine, deoxynojirimycine. Most preferred is the pharmaceutical composition wherein said protease inhibitor is darunavir or saquinavir. Even more preferred is the pharmaceutical composition wherein the compound has the formula (IIa) and the protease inhibitor is darunavir.

Compounds having the formula (I) or (II) or the respective pharmaceutical composition as defined above are used for the manufacture of a medicament for improving the pharmacokinetics of a drug, preferably for the inhibition of cytochrome P450 activity in a human being.

An object of the invention is also the use of an HIV protease inhibitor which is metabolized by cytochrome P450 in the manufacture of a medicament for the inhibition of cytochrome P450 activity in a human host in combination with compounds comprising the formula (I) or (II) or a pharmaceutically acceptable salt thereof, wherein the amount of said compounds having the formula (I) or (II) is sufficient to improve the pharmacokinetics of the HIV protease inhibitor in a patient, relative to the pharmacokinetics of the HIV protease inhibitor when administered alone.

Another object of the invention is a pharmaceutical kit comprising a pharmaceutical composition having compounds with the formula (I) or (II) more preferably (IIa), (IIb), (IIc) or (IId) and most preferably (IIa), a pharmaceutically acceptable carrier and a drug which is metabolized by cytochrome P450. The drug metabolized by cytochrome P450 is a HIV protease inhibitor such as darunavir or saquinavir.

An object of the invention is also a method for improving the pharmacokinetics of a drug which is metabolized by cytochrome P450 comprising administering to a human host in need of such treatment a therapeutically effective amount of a combination of said drug or a pharmaceutically acceptable salt thereof and compounds comprising formula (I) or (II), an N-oxide, salt, stereo-isomeric form or prodrug, or a pharmaceutically acceptable salt thereof.

Another object of the invention is a method for inhibiting cytochrome P450 comprising administering to a human host in need thereof an amount of the compounds comprising formula (I) or (II), an N-oxide, salt, stereo-isomeric form or prodrug, or a pharmaceutically acceptable salt thereof effective to inhibit cytochrome P450.

For therapeutic use, the salts of compounds of formula (I) or (II) are those wherein the counter ion is pharmaceutically or physiologically acceptable. However, salts having a pharmaceutically unacceptable counter ion may also find use, for example, in the preparation or purification of a pharmaceutically acceptable compound of formula (I) or (II). All salts, whether pharmaceutically acceptable or not are included within the ambit of the present invention.

The pharmaceutically acceptable or physiologically tolerable addition salt forms, which the compounds used in the present invention are able to form, can conveniently be prepared using the appropriate acids, such as, for example, inorganic acids such as hydrohalic acids, e.g. hydrochloric or hydrobromic acid; sulfuric; hemisulphuric, nitric; phosphoric and the like acids; or organic acids such as, for example, acetic, aspartic, dodecylsulphuric, heptanoic, hexanoic, nicotinic, propanoic, hydroxyacetic, lactic, pyruvic, oxalic, malonic, succinic, maleic, fumaric, malic, tartaric, citric, methane-sulfonic, ethanesulfonic, benzenesulfonic, p-toluenesulfonic, cyclamic, salicylic, p-aminosalicylic, pamoic and the like acids.

Conversely said acid addition salt forms can be converted by treatment with an appropriate base into the free base form.

The compounds of formula (I) or (II) containing an acidic proton may also be converted into their non-toxic metal or amine addition salt form by treatment with appropriate organic and inorganic bases. Appropriate base salt forms comprise, for example, the ammonium salts, the alkali and earth alkaline metal salts, e.g. the lithium, sodium, potassium, magnesium, calcium salts and the like, salts with organic bases, e.g. the benzathine, N-methyl, -D-glucamine, hydrabamine salts, and salts with amino acids such as, for example, arginine, lysine and the like.

Conversely said base addition salt forms can be converted by treatment with an appropriate acid into the free acid form.

The term "salts" also comprises the hydrates and the solvent addition forms, which the compounds of the present invention are able to form. Examples of such forms are e.g. hydrates, alcoholates and the like.

The present compounds used in the present invention may also exist in their N-oxide forms of formula (I) or (II) wherein one or several nitrogen atoms are oxidized to the so-called N-oxide.

The present compounds used in the invention may also exist in their tautomeric forms. Such forms, although not explicitly indicated in the above formula are intended to be included within the scope of the present invention.

The present compound used in the current invention may also exist in their stereo-chemically isomeric form, defining all possible compounds made up of the same atoms bonded by the same sequence of bonds but having different three-dimensional structures, which are not interchangeable. Unless otherwise mentioned or indicated, the chemical designation of compounds encompasses the mixture of all possible stereochemically isomeric forms, which said compounds might possess.

Said mixture may contain all diastereomers and/or enantiomers of the basic molecular structure of said compound. All stereochemically isomeric forms of the compounds used in the present invention either in pure form or in admixture with each other are embraced within the scope of the present invention.

Pure stereoisomeric forms of the compounds and intermediates as mentioned herein are defined as isomers substantially free of other enantiomeric or diastereomeric forms of the same basic molecular structure of said compounds or intermediates. In particular, the term 'stereoisomerically pure' concerns compounds or intermediates having a stereoisomeric excess of at least 80% (i.e. minimum 90% of one isomer and maximum 10% of the other possible isomers) up to a stereoisomeric excess of 100% (i.e. 100% of one isomer and none of the other), more in particular, compounds or intermediates having a stereoisomeric excess of 90% up to 100%, even more in particular having a stereoisomeric excess of 94% up to 100% and most in particular having a stereoisomeric excess of 97% up to 100%. The terms 'enantiomerically pure' and 'diastereomerically pure' should be understood in a similar way, but then having regard to the enantiomeric excess, respectively the diastereomeric excess of the mixture in question.

Pure stereoisomeric forms of compounds and intermediates used in this invention may be obtained by the application of art-known procedures. For instance, enantiomers may be separated from each other by the selective crystallization of their diastereomeric salts with optically active acids or bases. Examples thereof are tartaric acid, dibenzoyltartaric acid, ditoluoyltartaric acid and camphosulfonic acid. Alternatively, enantiomers may be separated by chromatographic techniques using chiral stationary phases. Said pure stereochemically isomeric forms may also be derived from the corresponding pure stereochemically isomeric forms of the appropriate starting materials, provided that the reaction occurs stereospecifically. Preferably, if a specific stereoisomer is desired, said compound will be synthesized by stereospecific methods of preparation. These methods will advantageously employ enantiomerically pure starting materials.

It is clear to a person skilled in the art that compounds of formula (I) or (II) contains two asymmetric centers and thus may exist as different stereoisomeric forms. This asymmetric center is indicated with an asterisk (*) in the figure below for formula (I)

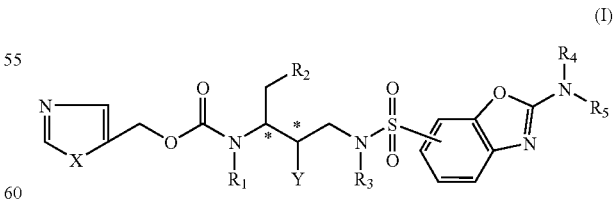

The absolute configuration of each asymmetric center that may be present in the compounds of formula (I) may be indicated by the stereochemical descriptors R and S, this R and S notation corresponding to the rules described in Pure Appl. Chem. 1976, 45, 11-30. The same is applicable to formula (II).

The present invention is also intended to include all isotopes of atoms occurring on the present compounds. Isotopes include those atoms having the same atomic number but different mass numbers. By way of general example and without limitation, isotopes of hydrogen include tritium and deuterium. Isotopes of carbon include C-13 and C-14.

The present compounds can thus be used in animals, preferably in mammals, and in particular in humans as pharmaceuticals per se, in mixtures with one another or in the form of pharmaceutical preparations.

The present invention relates to pharmaceutical preparations, which as active constituent contains an effective dose of compounds of formula (I) or (II), more preferably (IIa) and a drug which is metabolized by cytochrome P450, in addition to customary pharmaceutically innocuous excipients and auxiliaries. The pharmaceutical preparations can be prepared in a manner known per se to one of skill in the art. For this purpose compound of formula (IIa) together with one or more solid or liquid pharmaceutical excipients and/or auxiliaries and, if desired, in combination with other pharmaceutical active compounds, is brought into a suitable administration form or dosage form which can then be used as a pharmaceutical in human medicine or veterinary medicine.

The person skilled in the art is familiar on the basis of his expert knowledge with the auxiliaries, which are suitable for the desired pharmaceutical formulation. Beside solvents, gel-forming agents, suppository bases, tablet auxiliaries and other active compound carriers, antioxidants, dispersants, emulsifiers, antifoams, flavor corrigents, preservatives, solubilizers, agents for achieving a depot effect, buffer substances or colorants are also useful.

Pharmaceuticals containing those compounds are administered orally, parenterally, e.g., intravenously, rectally, by inhalation, or topically, the preferred administration being dependent on the individual case, e.g., the particular course of the disorder to be treated. Oral administration is preferred.

For an oral administration form, the compounds are mixed with suitable additives, such as excipients, stabilizers or inert diluents, and brought by means of the customary methods into the suitable administration forms, such as tablets, coated tablets, hard capsules, aqueous, alcoholic, or oily solutions. Examples of suitable inert carriers are gum arabic, magnesia, magnesium carbonate, potassium phosphate, lactose, glucose, or starch, in particular, corn starch. In this case the preparation can be carried out both as dry and as moist granules. Suitable oily excipients or solvents are vegetable or animal oils, such as sunflower oil or cod liver oil. Suitable solvents for aqueous or alcoholic solutions are water, ethanol, sugar solutions, or mixtures thereof. Polyethylene glycols and polypropylene glycols are also useful as further auxiliaries for other administration forms.

For subcutaneous or intravenous administration, the active compounds, if desired with the substances customary therefor such as solubilizers, emulsifiers or further auxiliaries, are brought into solution, (nano)suspension, or emulsion. The compound of formula (IIa) can also be lyophilized and the lyophilizates obtained used, for example, for the production of injection or infusion preparations. Suitable solvents are, for example, water, physiological saline solution or alcohols, e.g. ethanol, propanol, glycerol, in addition also sugar solutions such as glucose or mannitol solutions, or alternatively mixtures of the various solvents mentioned.

Suitable pharmaceutical formulations for administration in the form of aerosols or sprays are, for example, solutions, suspensions or emulsions of the compound of formula (IIa) or their physiologically tolerable salts in a pharmaceutically acceptable solvent, such as ethanol or water, or a mixture of such solvents. If required, the formulation can also additionally contain other pharmaceutical auxiliaries such as surfactants, emulsifiers and stabilizers as well as a propellant. Such a preparation customarily contains the active compound in a concentration from approximately 0.1 to 50%, in particular from approximately 0.3 to 3% by weight.

In particular, the present compounds may be formulated in a pharmaceutical composition comprising a therapeutically effective amount of particles consisting of a solid dispersion comprising (a) a compound of formula (IIa), and (b) one or more pharmaceutically acceptable water-soluble or water-insoluble polymers.

The term "a solid dispersion" defines a system in a solid state (as opposed to a liquid or gaseous state) comprising at least two components, wherein one component is dispersed more or less evenly throughout the other component or components. When said dispersion of the components is such that the system is chemically and physically uniform or homogenous throughout or consists of one phase as defined in thermo-dynamics, such a solid dispersion is referred to as "a solid solution". Solid solutions are preferred physical systems because the components therein are usually readily bioavailable to the organisms to which they are administered.

The term "a solid dispersion" also comprises dispersions, which are less homogenous throughout than solid solutions. Such dispersions are not chemically and physically uniform throughout or comprise more than one phase.

The water-soluble polymer in the particles is conveniently a polymer that has an apparent viscosity of 1 to 100 mPa·s when dissolved in a 2% aqueous solution at 20° C. solution.

Preferred water-soluble polymers are hydroxypropyl methylcellulose (HPMC) or hydroxypropyl methylcellulose acetate succinate (HPMC-AS). HPMC having a methoxy degree of substitution from about 0.8 to about 2.5 and a hydroxypropyl molar substitution from about 0.05 to about 3.0 is generally water soluble. Methoxy degree of substitution refers to the average number of methyl ether groups present per anhydroglucose unit of the cellulose molecule. Hydroxypropyl molar substitution refers to the average number of moles of propylene oxide, which have reacted with each anhydroglucose unit of the cellulose molecule.

The particles as defined hereinabove can be prepared by first preparing a solid dispersion of the components, and then optionally grinding or milling that dispersion. Various techniques exist for preparing solid dispersions including melt-extrusion, spray-drying and solution-evaporation.

The route of administration may depend on the condition of the subject, co-medication and the like.

The dose of the present compounds or of the physiologically tolerable salt(s) thereof to be administered depends on the individual case and, as customary, is to be adapted to the conditions of the individual case for an optimum effect. Thus it depends, of course, on the frequency of administration and on the potency and duration of action of the compounds employed in each case for therapy or prophylaxis, but also on the nature and severity of the infection and symptoms, and on the sex, age, weight, co-medication, and individual responsiveness of the human or animal to be treated and on whether the therapy is acute or prophylactic. The dose can be administered in the form of an individual dose, or divided into several, e.g. two, three, or four, individual doses.

Another aspect of the current invention concerns a kit or container comprising a compound of formula (IIa) optionally together with a protease inhibitor like, saquinavir or darunavir, in an amount effective for use as a standard or reagent in a test or assay for determining the ability of a potential pharmaceutical to inhibit HIV protease, HIV growth or both. This aspect may find its use in pharmaceutical research programs. Alternatively compounds having formula (IIa) can be formulated with a protease inhibitor, either darunavir or saquinavir, in one pill, tablet or syringe for treatment of a patient diagnosed of AIDS/HIV infection.

EXAMPLES

1. Preparation of 5-thiazolylmethyl [(1S,2R)-3[[(2-amino-6-benzoxazolyl)sulfonyl](2-methylpropyl)amino]-2-hydroxy-1-phenylmethyl)propyl]carbamate A typical method to prepare 5-thiazolylmethyl [(1S,2R)-3[[(2-amino-6-benzoxazolyl)sulfonyl](2-methylpropyl)amino]-2-hydroxy-1-phenylmethyl)propyl]carbamate (compound 1-4) is disclosed in WO 02/092595 and involves the following steps:

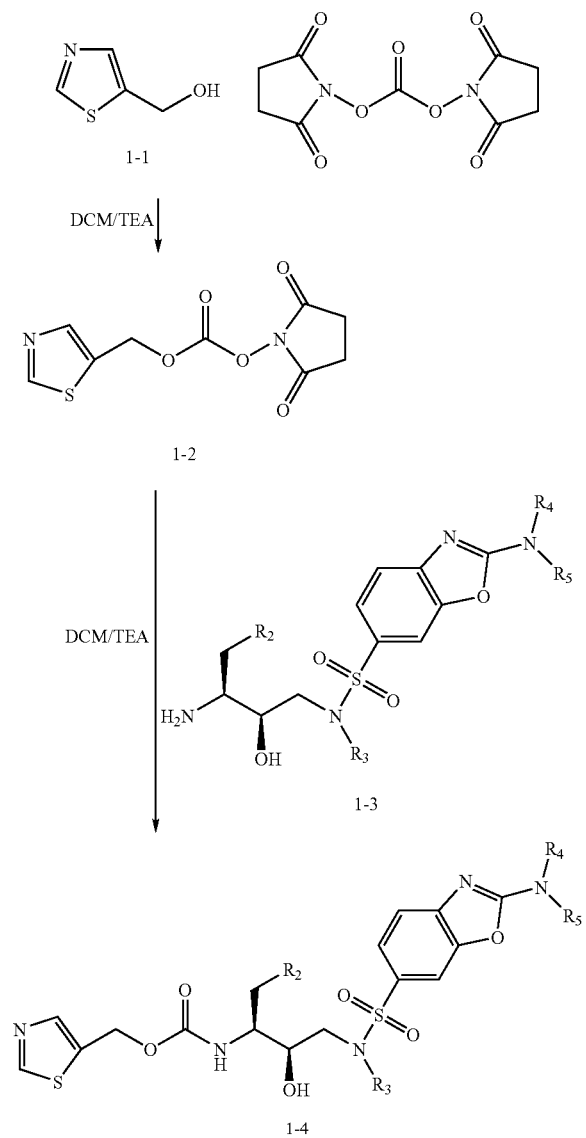

A mixture of 1.15 g of thiazol-5-yl-methanol (1-1) and 1.2 g triethylamine (TEA) in 25 ml of dichloromethane (DCM) was stirred at room temperature under an atmosphere of nitrogen. 2.56 g of N,N'-disuccinimidyl carbonate was then added and the resulting mixture was stirred for 10-15 minutes. The solution was stirred for an additional 2 hours. The resulting intermediate (1-2) was used directly in the subsequent reaction with the amine (1-3). Instead of amines also salts thereof can be used.

Triethylamine 2 g and the amine 5 g (1-3), wherein $R_2$ is phenyl; $R_3$ is iso-butyl; $R_4$ is hydrogen and $R_5$ is hydrogen, were added to dichloromethane 40 ml and the resulting mixture was stirred at room temperature. Subsequently, a portion of the solution comprising 1-2 was added drop wise. The reaction mixture was stirred at room temperature for 2 hours. The reaction mixture was washed with water and then dried to yield compound (1-4). The stereo isomers of compound (1-4) were prepared in an analogous chemical process.

Compound (1-4), when $R_2$ is phenyl; $R_3$ is iso-butyl; $R_4$ is hydrogen and $R_5$ is hydrogen and thus is represented by formula (IIa), has been analyzed.

All reagents, were purchased from commercial sources (Acros, Aldrich or Fluorochem) and were used as received. NMR spectra were recorded on a Bruker Avance 400 spectrometer, operating at 400 MHz for $^1$H with CDCl$_3$ as solvent. In each case tetramethylsilane (TMS) was used as internal standard. Chemical shifts are given in ppm. Multiplicity is indicated using the following abbreviations: d for doublet, t for a triplet, m for a multiplet, etc. Low-resolution mass spectra (LRMS) were performed on an ion trap (ThermoFinnigan LCQ Deca) or a time of flight (Waters LCT) mass spectrometer using electrospray ionization (ESI) in positive mode. Column chromatography was carried out on silica gel 60 Å, 60-200 μm (ROCC). Thin layer chromatography was performed on silica gel 60 $F_{254}$ plates (Merck). Analytical HPLC was done on a Waters Alliance 2690 (pump+auto sampler) system equipped with a Waters 996 photo diode array-detector. To check the purity of the end products the following chromatographic system was used. Column: Waters Xterra MS C18, (3.5 μm, 4.60 mm×100 mm), mobile phase A: 10 mM $CH_3COONH_4$ in $H_2O$, mobile phase B: $CH_3CN$. Analysis were run at 30° C. using a flow rate of 1 mL/min applying the following gradient: 0 min: 5% B, 10 min: 95% B, 12 min: 95% B. In every case, 10 μl of a 1 mM solution was injected. The equilibration time between two runs was 3 minutes. Eluted peaks were detected at a single wavelength ($\lambda_{max}$). The retention time is reported in minutes.

Data for (IIa):

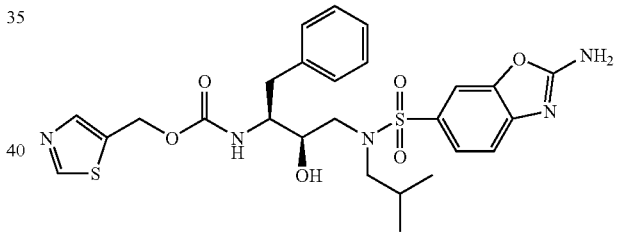

$^1$H-NMR (400 MHz) ppm 8.75 (s, 1H, H1); 7.80 (s, 1H, H2); 7.67 (d, 1H, J=1.6 Hz, H18); 7.61 (dd, 1H, J=1.7 Hz, J=8.3 Hz, H16); 7.39 (d, 1H, J=8.3 Hz, H17); 7.23 (m, 5H, H7, H8, H9); 5.60 (s, 2H, H19); 5.25 (d, 1H, J=13.6 Hz, H3'); 5.15 (d, 1H, J=13.0 Hz, H3); 5.00 (d, 1H. J=7.4 Hz, H4); 3.86 (br s, 2H, H5, H10); 3.68 (br s, 1H, H11); 2.96 (m, 6H, H6, H6', H12, H12', H13, H13'); 1.81 (m, 1H, H14); 0.87 (m, 6H, H15)

LRMS: m/z: 574

Purity determination: Rt=7.51 min, purity: 99.06%

Data for (IIb):

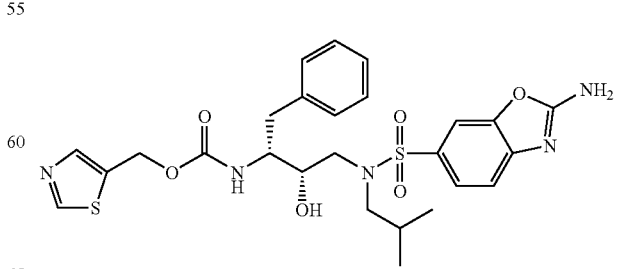

LRMS: m/z: 574

Purity determination: Rt=6.94 min, purity: 97.55%

Data for (IIc)

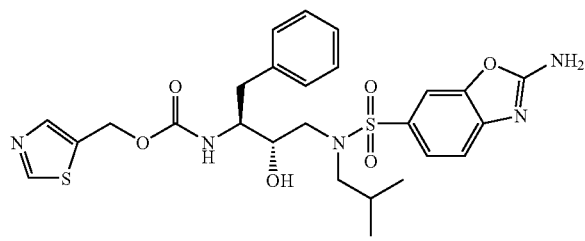 [SMILES: CC(C)CN(C[C@H](O)[C@H](Cc1ccccc1)NC(=O)OCc1cncs1)S(=O)(=O)c1ccc2nc(N)oc2c1]

LRMS: m/z: 574
Purity determination: Rt=7.27 min, purity: 96.56%

On Day 1 in all panels, all subjects received a single dose of 1000 mg saquinavir. From Day 4 to Day 10, one group of healthy volunteers (Panel 1) received 60 mg compound A b.i.d., one group received 160 mg compound A b.i.d. (Panel 2) and one group took 400 mg compound A b.i.d. (Panel 3). On Day 9, all subjects took a single dose of 1000 mg saquinavir simultaneously with compound A. Full pharmacokinetic profiles of compound A were determined on Day 4, Day 8 and Day 9. Full pharmacokinetic profiles of saquinavir were determined on Day 1 and on Day 9. The results of the study are summarized in the table below.

Pharmacokinetic Parameters (Mean±SD) of Saquinavir in the Absence (Day 1) and in the Presence of Compound A (Day 9)

| Pharmacokinetic parameters of saquinavir (mean values ± SD, for $t_{max}$: median (range)) | Treat A: 60 mg compound A b.i.d. 1000 mg SQV. SD | Treat B: 160 mg compound A b.i.d. 1000 mg SQV, SD | Treat C: 400 mg compound A b.i.d. 1000 mg SQV, SD |
|---|---|---|---|
| Day 1 | | | |
| n | 8 | 8 | 8 |
| $C_{max}$, ng/mL | 117.0 ± 77.74 | 101.7 ± 47.75 | 104.4 ± 73.32 |
| $t_{max}$, h | 4.5 (2.0-6.0) | 5.0 (2.0-6.0) | 5.0 (2.0-6.0) |
| $AUC_{last}$, ng · h/mL | 514.8 ± 306.3 | 440.8 ± 198.5 | 415.2 ± 267.5 |
| Day 9 | | | |
| n | 8 | 8 | 7 |
| $C_{max}$, ng/mL | 2011 ± 544.9 | 2190 ± 951.2 | 1821 ± 1150 |
| $t_{max}$, h | 6.0 (4.0-6.0) | 4.0 (4.0-6.0) | 6.0 (3.0-6.0) |
| $AUC_{last}$, ng · h/mL | 11278 ± 3722 | 14872 ± 7658 | 11790 ± 7457 |

2. Effects of 5-thiazolylmethyl [(1S,2R)-3[[(2-amino-6-benzoxazolyl)sulfonyl](2-methylpropyl)amino]-2-hydroxy-1-phenylmethyl)propyl]carbamate on the pharmacokinetics of the protease inhibitor saquinavir in healthy male volunteers Compound 5-thiazolylmethyl [(1S,2R)-3[[(2-amino-6-benzoxazolyl)sulfonyl](2-methylpropyl)amino]-2-hydroxy-1-phenylmethyl)propyl]carbamate (further referred to as compound A) and represented by the chemical formula:

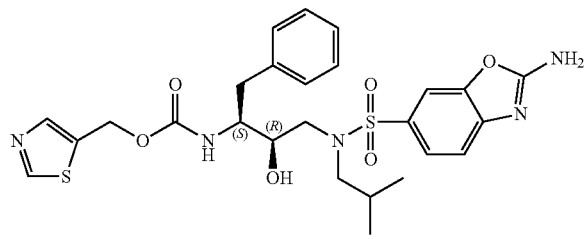

was used in a Phase I, open-label, randomized trial in healthy subjects to investigate the steady state pharmacokinetics of compound A, and its effect on the single dose pharmacokinetics of the protease inhibitor saquinavir. Three panels of 8 healthy subjects took a single dose of 1000 mg saquinavir alone, and while taking compound A. The pharmacokinetics of the two intakes of saquinavir was compared.

These results demonstrate that compound A substantially enhances the pharmacokinetics of saquinavir, with overall exposures expressed as AUC increased over 20-fold for all of the compound A dose levels evaluated.

3. In Vitro Inhibition of Cytochrome P450, Specifically CYP3A4

The inhibition constant, $K_i$ of compound A on testosterone metabolism mediated by CYP450 3A4 in human liver microsomes was studied. The result from this experiment showed that compound A is a potent inhibitor of 6β-hydroxylation of testosterone. In the experiments compound A was as potent as ritonavir as an inhibitor of CYP3A4 mediated metabolism with an $IC_{50}$ between 100 and 25 nM.

The mode of CYP3A4 inhibition by compound A can be described by a non-competitive inhibition model with an inhibition constant Ki of 65 nM. The $K_m$ values could not be established for the metabolism using human, rat and dog microsomes despite successive incubations at lower concentrations. At the lowest concentration tested (50 nM) the rate of compound A metabolism was still similar to the rate observed at 10 μM.

4. Effects of Compound A on Protease Inhibitor Transport Across Caco-2 Monolayers The transport of experimental protease inhibitors was studied in Caco-2 monolayers grown to confluency. (Augustijns et al. (1998). *Int. J of Pharm,* 166, 45-54). After cell monolayer integrity confirmation, the experimental HIV protease inhibitors, as described in WO 02/083657, compound B and compound C (chemical structures given below) were applied to either the apical (AP) or the basolateral (BL) side of the cell monolayers in order to study transport in the AP to BL and BL to AP direction, respectively. The effects of compound A and the P-glycoprotein (Pgp) inhibitor verapamil (100 µM) on the bi-directional transport were measured.

Results are summarized in the table below:

TABLE

Comparison of efflux ratio (ER) values (90 min) in the absence and presence of Verapamil and compound A (100 µM) for the experimental protease inhibitors compound B and compound C (30 µM)

|  | Compound B | Compound C |
|---|---|---|
| Control | 171 | 119 |
| Verapamil | 6.2 | 8.7 |
| Compound A | 7.5 | 8.3 |

The profile was very comparable between the 2 protease inhibitors, that all showed very high transport polarity with the secretory transport highly exceeding the absorptive transport at low concentrations (3-30 µM).

Verapamil, a well-established marker inhibitor of Pgp, and compound A significantly reduce the transport polarity. Verapamil and compound A are equipotent in reducing efflux, which clearly suggests that compound A is an inhibitor of Pgp.

5. In Vivo Effects of Compound A on the Pharmacokinetics of Darunavir in Rabbits The ability of compound A to enhance the pharmacokinetics of darunavir, a novel PI under investigation for the treatment of HIV-infections, was evaluated in rabbits. Female rabbits were selected as a model species as the metabolite profile for darunavir resembles that in humans, and since it appeared to be a representative and sensitive animal model to study the effect of boosting of the bioavailability of darunavir. Four rabbits were orally dosed with 20 mg/kg compound A at 0 and 6 hours on 2 successive days. On the second day, the 0-hour dose of compound A was immediately followed by a single oral dose of 500 mg/kg darunavir.

The pharmacokinetic parameters for darunavir after oral dosing with and without compound A, are summarized in the Table below.

Treatment with compound A resulted in a highly increased pharmacokinetics of the co-administered protease inhibitor, darunavir. The average increase in the $C_{max}$ of darunavir with and without compound A, with mean values of 10.1 µg/mL, and 0.34 µg/mL, respectively, was 38-fold. The mean $AUC_{0-24h}$ of darunavir in the presence of compound A was 25.7 µg·h/mL, compared to 2.2 µg·h/mL when darunavir was given alone.

The relative bioavailability of darunavir dosed in combination with compound A was determined by calculating the ratios of the AUCs of darunavir after dosing with compound A and the AUCs after dosing darunavir alone, in the same animals. The average pharmacokinetics of darunavir dosed in combination with compound A was 13-fold increased.

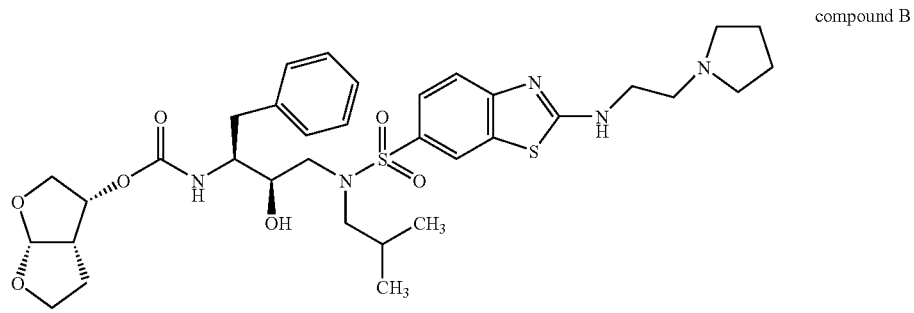

compound B

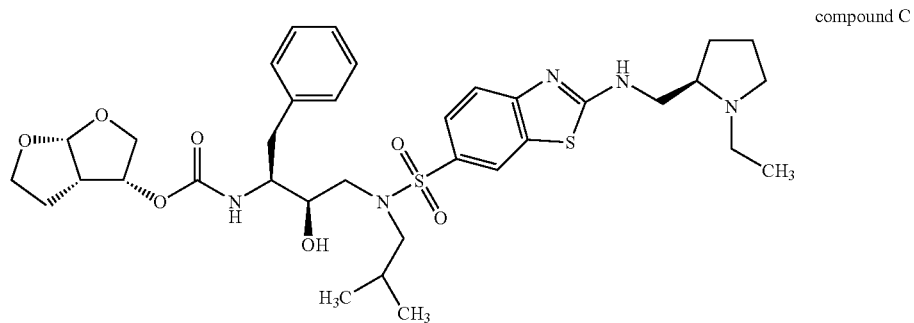

compound C

TABLE 1

Pharmacokinetic parameters of darunavir in rabbits after a single dose of 500 mg/kg darunavir, with and without co-administration of 20 mg b.i.d. compound A

| Parameter (unit) | darunavir alone | | | Darunavir + compound A | | | Ratios +/− Compound A |
|---|---|---|---|---|---|---|---|
| | Mean | SD | CV % | Mean | SD | CV % | |
| $C_{max}$ (ng/mL) | 341 | 231 | 67.6 | 10120 | 3357 | 33.2 | 38 |
| $T_{max}$ (h) | 1.8 | 1.7 | 94.8 | 0.88 | 0.25 | 29 | — |
| $t_{1/2}$ (h) | 10.3 | 5.4 | 53 | 35 | $NC^a$ | $NC^a$ | — |
| $AUC_{0-24\,h}$ (ng·h/mL) | 2222 | 1026 | 46.2 | 25667 | 12288 | 47.9 | 13 |

SD: standard deviation
[a]NC; not calculated $C_{24\,h} > C_{8\,h}$
CV: coefficient of variation A second study in rabbits was performed to compare the effect of a range of oral doses of compound A and the effect of a single dose of compound E, an enantiomer (formula IIb) of compound A, as boosting agents on the bioavailability of darunavir. Three groups of 3 female NZW rabbits were dosed with a single dose of 500 mg/kg of darunavir, either alone, with a single oral dose of 20 mg/kg of compound A or with a single oral dose of 20 mg/kg compound E (period I).

In period II, compound A was dosed twice daily for 2 days at 4 mg/kg, at 10 mg/kg or 20 mg/kg, with a single dose of 500 mg/kg darunavir in the morning of the $2^{nd}$ day.

The darunavir pharmacokinetic parameters with the effects of compound A and its enantiomer compound E, and with the effects of varying doses of compound A are summarized in Table 2 and Table 3, respectively.

TABLE 2

Pharmacokinetic parameters of darunavir in rabbits after a single dose of 500 mg/kg darunavir, with and without co-administration of a single dose of 20 mg/kg compound A or its enantiomer, compound E

| | Group | | | | | | | | |
|---|---|---|---|---|---|---|---|---|---|
| | Control | | | Compound A (20 mg/kg) | | | Compound E (mg/kg) | | |
| Time (h) | Mean | SD | CV % | Mean | SD | CV % | Mean | SD | CV % |
| $C_{max}$ (ng/ml) | 187 | 100 | 53.6 | 12500 | 3040 | 24.4 | 8590 | 3270 | 38.0 |
| $T_{max}$ (h) | 0.67 | 0.29 | 43 | 1.0 | 0.0 | 0.0 | 1.3 | 0.6 | 43 |
| $t_{1/2}$ (h) | 12 | 9 | 72 | 20 | 9 | 43 | 15 | 14 | 95 |
| $AUC_{0-24\,h}$ (ng·h/ml) | 768 | 458 | 59.6 | 23800 | 9430 | 39.6 | 16800 | 4960 | 29.6 |
| Ratios vs. control | | | | | | | | | |
| $AUC_{0-24\,h}$ | | | | | 31 | | | 22 | |
| $C_{max}$ | | | | | 67 | | | 46 | |

TABLE 3

Pharmacokinetic parameters of darunavir in rabbits after a single dose of 500 mg/kg darunavir, with and without co-administration of either 4, 10 and 20 mg b.i.d. compound A

| | Dose of compound A | | | | | | | | | | | |
|---|---|---|---|---|---|---|---|---|---|---|---|---|
| | 0 (control) | | | 4 mg/kg bid | | | 10 mg/kg bid | | | 20 mg/kg bid | | |
| | Mean | SD | CV % | Mean | SD | CV % | Mean | SD | CV % | Mean | SD | CV % |
| $C_{max}$ (ng/ml) | 187 | 100 | 53.6 | 1590 | 979 | 61.6 | 7630 | 3780 | 49.6 | 13000 | 5900 | 45.3 |
| $T_{max}$ (h) | 0.67 | 0.29 | 43 | 1.2 | 0.8 | 66 | 1.0 | 0.0 | 0.0 | 1.0 | 0.0 | 0.0 |
| $t_{1/2}$ (h) | 12 | 9 | 72 | 27 | 14 | 54 | 13 | 0 | 2.3 | 5.1 | 2.1 | 41 |
| $AUC_{0-24\,h}$ (ng·h/ml) | 768 | 458 | 59.6 | 4050 | 2240 | 55.2 | 16300 | 10800 | 66.2 | 34700 | 13100 | 37.6 |
| Ratios vs. control | | | | | | | | | | | | |
| $AUC_{0-24\,h}$ | 1 | | | 5.3 | | | 21 | | | 45 | | |
| $C_{max}$ | 1 | | | 8.8 | | | 41 | | | 70 | | |

The results of these experiments in rabbits confirm that compound A is a potent enhancer of the pharmacokinetics of darunavir, with a dose dependent effect in the dose range from 4 to 20 mg/kg twice daily. Given as a single dose of 20 mg/kg simultaneous with darunavir, compound A boosted the pharmacokinetics of darunavir to a similar extent as the 20 mg/kg twice-daily regimen. Co-administration of a single dose of 20 mg/kg compound E (formula IIb), an enantiomer of compound A, also resulted in substantially (>20 fold) increased plasma concentrations of darunavir in rabbits.

6. In Vivo Effects of Compound A on the Pharmacokinetics of Darunavir in Primates A study in male cynomolgus monkeys was performed to evaluate the boosting effects of a dose range of compound A on the bioavailability of darunavir. This study in a primate species was expected to be most predictive for the effects in humans, from a pharmacokinetic perspective. Darunavir was given as a single dose of 40 mg/kg without or with compound A at dose levels of 0 control, 4, 10, 25 and 80 mg/kg. All dose groups consisted of 3 monkeys, except for the 80 mg/kg dose group with 4 animals included.

The effects of the range of dose levels for compound A on the darunavir pharmacokinetics, expressed as AUC, are depicted in FIG. 1.

FIG. 1: Mean dose-normalized darunavir AUC in cynomolgus monkeys (n=3-4 per dose group), versus boosting dose of compound A, in a dose range of 4 to 80 mg/kg/day, given as a twice-daily regimen for 2 days. Darunavir was given as a single dose of 40 mg/kg on day 2 of the experiment.

The results demonstrate that compound A substantially increases the pharmacokinetics of darunavir in cynomolgus monkeys, up from the low dose of 4 mg/kg (3.2 fold increased AUC), with an apparent maximal effect of around 15 fold at the high doses of 25 and 80 mg/kg. These data show that compound A is an efficient and potent booster of darunavir in this primate species.

7. Effect of Compound A on the Pharmacokinetics of the Protease Inhibitor Darunavir in Humans Compound A was used in an open-label, randomized trial in 3 panels of 8 healthy volunteers per panel to investigate its effect on the pharmacokinetics of the protease inhibitor darunavir. All subjects received the protease inhibitor darunavir at a dose level of 600 mg b.i.d. for 8 days with twice-daily coadministration of 30 mg, 60 mg or 120 mg compound A from day 4 onwards.

In all panels, coadministration of compound A considerably increased $AUC_{12h}$, $C_{max}$, and $C_{min}$ of darunavir. Increases in $C_{min}$ values were highest (up to 10 fold) and increases in $C_{max}$ were lowest (less than 2-fold). The increase in $AUC_{12h}$ was approximately 2-fold for Treatment A (30 mg compound A) and 3 to 4-fold for Treatment B (60 mg compound A) and C (120 mg compound A), suggesting that a maximal interaction effect by compound A had been reached at the 60 mg b.i.d. regimen.

This trial demonstrates that compound A is a potent booster for clinical use with darunavir.

The invention claimed is:

1. A method of improving the pharmacokinetics of HIV-aspartyl protease inhibitor drug darunavir or saquinavir metabolized by cytochrome P450, or inhibited by P-glycoprotein, MRP1 or MRP2 activity by administering an effective amount of a compound having the formula

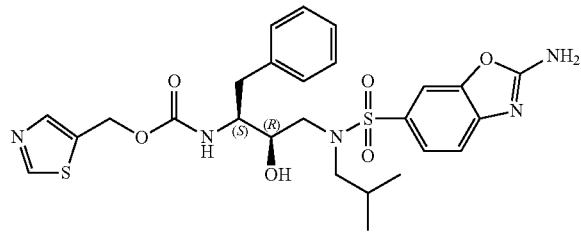

or a compound having the formula

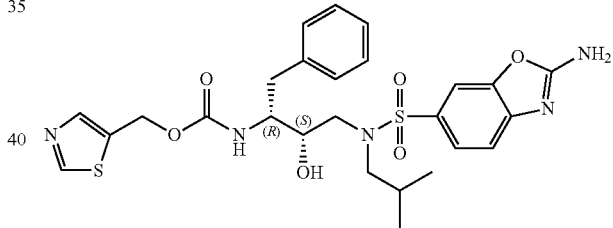

to a mammal in need of such improvement.

* * * * *

UNITED STATES PATENT AND TRADEMARK OFFICE
CERTIFICATE OF CORRECTION

PATENT NO.        : 8,557,854 B2                                      Page 1 of 1
APPLICATION NO.   : 11/911465
DATED             : October 15, 2013
INVENTOR(S)       : Van 'T Klooster et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 810 days.

Signed and Sealed this

Fifteenth Day of September, 2015

Michelle K. Lee
*Director of the United States Patent and Trademark Office*